(12) United States Patent
Nguyen et al.

(10) Patent No.: US 9,504,564 B2
(45) Date of Patent: *Nov. 29, 2016

(54) HEART VALVE PROSTHESIS AND METHODS OF MANUFACTURE AND USE

(75) Inventors: Than Nguyen, Fountain Valley, CA (US); Hung Nguyen, Garden Grove, CA (US); MyKim Nguyen, Santa Ana, CA (US); Stanley Komatsu, Laguna Hills, CA (US); Robrecht Michiels, Laguna Hills, CA (US)

(73) Assignee: Medtronic Corevalve LLC, Minneapolis, MN (US)

( * ) Notice: Subject to any disclaimer, the term of this patent is extended or adjusted under 35 U.S.C. 154(b) by 1551 days.

This patent is subject to a terminal disclaimer.

(21) Appl. No.: 11/433,296

(22) Filed: May 12, 2006

(65) Prior Publication Data

US 2006/0265056 A1 Nov. 23, 2006

Related U.S. Application Data

(63) Continuation-in-part of application No. 11/128,826, filed on May 13, 2005, now Pat. No. 7,914,569.

(51) Int. Cl.
*A61F 2/24* (2006.01)

(52) U.S. Cl.
CPC .......... *A61F 2/2412* (2013.01); *A61F 2/2418* (2013.01); *A61F 2/2415* (2013.01); *A61F 2220/005* (2013.01); *A61F 2220/0058* (2013.01); *A61F 2220/0075* (2013.01); *A61F 2230/008* (2013.01); *A61F 2230/0054* (2013.01);

(Continued)

(58) Field of Classification Search
USPC ......... 623/2.15, 2.17, 2.12, 2.26, 1.24, 1.26, 623/2.18
See application file for complete search history.

(56) References Cited

U.S. PATENT DOCUMENTS

| 3,334,629 A | 8/1967 | Cohn |
| 3,409,013 A | 11/1968 | Berry |
| 3,540,431 A | 11/1970 | Mobin-Uddin |

(Continued)

FOREIGN PATENT DOCUMENTS

| CN | 101011298 A | 8/2007 |
| DE | 19532846 | 3/1997 |

(Continued)

OTHER PUBLICATIONS

Balloon-Expandable Intracoronary Stent in the Adult Dog; Schatz, Richard MD et al.; *Laboratory Investigation—Myocardial Ischemia*, pp. 450-457 (1987).

(Continued)

*Primary Examiner* — Thomas J Sweet
*Assistant Examiner* — Megan Wolf

(57) ABSTRACT

A heart valve prosthesis is provided having a self-expanding multi-level frame that supports a valve body comprising a skirt and plurality of coapting leaflets. The frame transitions between a contracted delivery configuration that enables percutaneous transluminal delivery, and an expanded deployed configuration having an asymmetric hourglass shape. The valve body skirt and leaflets are constructed so that the center of coaptation may be selected to reduce horizontal forces applied to the commissures of the valve, and to efficiently distribute and transmit forces along the leaflets and to the frame. Alternatively, the valve body may be used as a surgically implantable replacement valve prosthesis.

25 Claims, 5 Drawing Sheets

(52) U.S. Cl.
CPC  *A61F2230/0067* (2013.01); *A61F 2250/0039* (2013.01); *Y10S 623/90* (2013.01)

(56) References Cited

U.S. PATENT DOCUMENTS

| | | |
|---|---|---|
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,833,458 A | 5/1989 | Bowman |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shurman |
| 5,327,774 A | 7/1994 | Nguyen et al. |
| 5,332,402 A | 7/1994 | Teitelbaum |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |

(56) References Cited

U.S. PATENT DOCUMENTS

| | | | |
|---|---|---|---|
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,327,772 B1 | 12/2001 | Zadno-Azizi et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,503,274 B1 | 1/2003 | Howanec et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,562,069 B2* | 5/2003 | Cai et al. ............... 623/2.12 |
| 6,569,196 B1 | 5/2003 | Vesely |
| 6,582,462 B1 | 6/2003 | Andersen et al. |
| 6,585,758 B1 | 7/2003 | Chouinard et al. |
| 6,585,766 B1* | 7/2003 | Huynh et al. ............ 623/2.38 |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens et al. |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,018,406 B2 | 3/2006 | Seguin et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,335,218 B2 | 2/2008 | Wilson et al. |
| 7,338,520 B2 | 3/2008 | Bailey et al. |
| 7,374,571 B2 | 5/2008 | Pease et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,556,646 B2 | 7/2009 | Yang et al. |
| 2001/0001314 A1 | 5/2001 | Davison et al. |
| 2001/0002445 A1 | 5/2001 | Vesely |

(56) References Cited

U.S. PATENT DOCUMENTS

| | | |
|---|---|---|
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2001/0049555 A1* | 12/2001 | Gabbay ............... 623/2.13 |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0069636 A1 | 4/2003 | Solem et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Sequin et al. |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1* | 10/2004 | Seguin et al. ............... 623/2.11 |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1* | 4/2005 | Cali ............... 600/587 |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075725 A1 | 4/2005 | Rowe |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096727 A1 | 5/2005 | Allen et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |

(56) References Cited

U.S. PATENT DOCUMENTS

| | | |
|---|---|---|
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1* | 9/2006 | Bonhoeffer et al. ......... 623/2.11 |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1* | 11/2006 | Nguyen et al. ............. 623/2.18 |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Jantz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Barlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0240320 A1 | 9/2009 | Tuval et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |

FOREIGN PATENT DOCUMENTS

| | | |
|---|---|---|
| DE | 195 46692 A1 | 6/1997 |
| DE | 19546692 | 6/1997 |
| DE | 19857887 | 7/2000 |
| DE | 19907646 | 8/2000 |
| DE | 10-049814 | 4/2002 |
| DE | 10-049815 | 4/2002 |
| DE | 10049812 | 4/2002 |
| DE | 10049813 | 4/2002 |
| EP | 0 103 546 A1 | 3/1984 |
| EP | 0 103 546 B1 | 3/1984 |
| EP | 0 597 967 | 12/1994 |
| EP | 0 850 607 | 7/1998 |
| EP | 1057459 A1 | 6/2000 |
| EP | 1 057 460 | 12/2000 |
| EP | 1 088 529 | 4/2001 |
| EP | 1255510 | 11/2002 |
| EP | 0937439 B1 | 9/2003 |
| EP | 1340473 | 9/2003 |
| EP | 0819013 | 6/2004 |
| FR | 1 271 508 A1 | 11/1986 |
| FR | 2 788 217 | 7/2000 |

(56) References Cited

FOREIGN PATENT DOCUMENTS

| | | |
|---|---|---|
| GB | 2 056 023 | 3/1981 |
| GB | 2433700 | 12/2007 |
| WO | WO 91/17720 | 11/1991 |
| WO | WO 92/17118 | 10/1992 |
| WO | WO 93/01768 | 2/1993 |
| WO | WO 93/18721 A1 | 9/1993 |
| WO | 95/29640 | 11/1995 |
| WO | 98/14137 | 4/1998 |
| WO | WO 98/29057 | 7/1998 |
| WO | WO 99/33414 | 7/1999 |
| WO | WO 00/41652 | 7/2000 |
| WO | 00/44313 | 8/2000 |
| WO | 00/47136 | 8/2000 |
| WO | WO 00/47139 | 8/2000 |
| WO | WO 01/06959 A1 | 2/2001 |
| WO | WO 01/35870 A1 | 5/2001 |
| WO | WO 01/49213 | 7/2001 |
| WO | WO01/49213 | 7/2001 |
| WO | WO 01/54625 | 8/2001 |
| WO | WO 01/62189 | 8/2001 |
| WO | WO 01/64137 | 9/2001 |
| WO | WO 01/76510 | 10/2001 |
| WO | WO 02/22054 | 5/2002 |
| WO | WO 02/36048 A1 | 5/2002 |
| WO | WO 02/41789 | 5/2002 |
| WO | WO 02/43620 | 6/2002 |
| WO | WO 02/47575 | 6/2002 |
| WO | WO 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | WO03/047468 | 6/2003 |
| WO | WO2004/016200 | 2/2004 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |
| WO | 2005/011534 | 2/2005 |
| WO | 2005/027790 | 3/2005 |
| WO | 2005/046528 | 5/2005 |
| WO | 2008/047354 | 4/2008 |
| WO | 2008/100599 | 8/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/061389 | 5/2009 |
| WO | 2009/091509 | 7/2009 |

OTHER PUBLICATIONS

Pelton et al, Medical Uses of Nitinol, Materials Science Forum vols. 327-2328 pp. 63-70. (2000).
U.S. Appl. No. 12/050,184, filed Mar. 18, 2008.
U.S. Appl. No. 12/050,628, filed Mar. 18, 2008.
U.S. Appl. No. 12/248,776, filed Oct. 9, 2008.
U.S. Appl. No. 12/250,163, filed Oct. 13, 2008.
U.S. Appl. No. 61/192,199, filed Sep. 15, 2008.
U.S. Appl. No. 12/253,858, filed Oct. 17, 2008.
U.S. Appl. No. 60/907,907, filed Apr. 20, 2007.
U.S. Appl. No. 61/129,170, filed Jun. 9, 2008.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Technique and Results of Percutaneous Mitral Valvuloplasty With the Multi-Track System," Journal of Interventional Cardiology (United States), 200, pp. 263-268.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-6.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-6.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.

(56) References Cited

OTHER PUBLICATIONS

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England); Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-1V-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Ruiz, "Transcatheter Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Yonga, et al, "Effect of Percutaneous Balloon-Mitral Valvotomy on Pulmonary Venous Flow in Severe Mitral Stenosis," East African Medical Journal (Kenya), Jan. 1999, pp. 28-30.
Yonga, et al, "Percutaneous Balloon Mitral Valvotomy: Initial Experience in Nairobi Using a New Multi-Track Catheter System," East African Medical Journal (Kenya), Feb. 1999, pp. 71-74.
Yonga, et al, "Percutaneous Transluminal Balloon Valvuloplasty for Pulmonary Valve Stenosis: Report on Six Cases," East African Medical Journal (Kenya), Apr. 1994, pp. 232-235.
Yonga, et al, "Percutaneous Transvenous Mitral Commissurotomy in Juvenile Mitral Stenosis," East African Medical Journal (Kenya), Apr. 2003, pp. 172-174.
Commeau et al, "Percutaneous balloon dilatation of calcific aortic valve stenosis: anatomical and haemodynamic evaluation," 1988, British Heart Journal, 59:227-238.
Stassano et al., "Mid-term results of the valve-on-valve technique for bioprosthetic failure," Eur. J. Cardiothorac. Surg. 2000; 18:453-457.
Expert report of Dr. Nigel Buller, dated Jan. 12, 2009, Edwards' United Kingdom action for invalidity, Claim No. HC 08CO0934.
Expert report of Dr. Nigel Buller, non-confidential annex—infringement, dated Jan. 12, 2009, Edwards' United Kingdom action for invalidity, Claim No. HC 08CO0934.
Expert report of Dr. Rodolfo Quijano, dated Jan. 9, 2009, Edwards' United Kingdom action for invalidity, Claim No. HC 08CO0934.
First Expert report of Prof. David Williams, dated Jan. 12, 2009, Edwards' United Kingdom action for invalidity, Claim No. HC 08CO0934.
First Expert report of Prof. Martin Rothman, dated Jan. 12, 2009, Edwards' United Kingdom action for invalidity, Claim No. HC 08CO0934.
Fourth Expert report of Prof. Martin Rothman, dated Apr. 22, 2009, Edwards' United Kingdom action for invalidity, Claim No. HC 08CO0934.
Second Expert report of Dr. Nigel Buller, dated Feb. 25, 2009, Edwards' United Kingdom action for invalidity, Claim No. HC 08CO0934.
Second Expert report of Dr. Rodolfo Quijano, dated Feb. 26, 2009, Edwards' United Kingdom action for invalidity, Claim No. HC 08CO0934.
Second Expert report of Prof. David Williams, dated Feb. 5, 2009, Edwards' United Kingdom action for invalidity, Claim No. HC 08CO0934.
Second Expert report of Prof. Martin Rothman, dated Feb. 5, 2009, Edwards' United Kingdom action for invalidity, Claim No. HC 08CO0934.
Third Expert report of Dr. Nigel Buller, dated Apr. 21, 2009, Edwards' United Kingdom action for invalidity, Claim No. HC 08CO0934.
Third Expert report of Dr. Rudolfo Quijano, dated Apr. 27, 2009, Edwards' United Kingdom action for invalidity, Claim No. HC 08CO0934.
Third Expert report of Prof. David Williams, dated Apr. 22, 2009, Edwards' United Kingdom action for invalidity, Claim No. HC 08CO0934.
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Second Expert report of Dr. Nigel Person Buller (5 pages), *Corevalve, Inc.* v. *Edwards Lifesciences AG and Edwards Lifesciences PVT, Inc.*, High Court of Justice —Chancery Division Patents Court, United Kingdom, Case No. HC-07-C01243.
Drawing by Dr. Buller (Edwards Expert) of his interpretation of the "higher stent" referred to at col. 8, lines 13-222 of Andersen EP 592410B1 (1 page), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of "higher stent" on the schematic representation of the aortic valve area set out in Figure 2 of Rothman's first expert report (1 page), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Professor John R. Pepper (20 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Second Expert report of Professor John R. Pepper (3 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Dr. Anthony C. Lunn (7 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Witness statement of Stanton Rowe (9 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.

(56) References Cited

OTHER PUBLICATIONS

Second Witness statement of Stanton Rowe (3 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
PVT slides naming Alain Cribier, Martin Leon, Stan Rabinovich and Stanton Rowe (16 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Professor Martin Terry Rothman (75 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Reply Expert report of Professor Martin Terry Rothman (9 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
First Expert report of Richard A. Hillstead (41 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Reply Expert report of Richard A. Hillstead (9 pages), *Corevalve, Inc.* v. *Edwards Lifesciences AG and Edwards Lifesciences PVT, Inc.*, High Court of Justice—Chancery Division Patents Court, United Kingdom, Case No. HC-07-C01243.
U.S. Appl. No. 10/772,101, filed Feb. 4, 2004.
U.S. Appl. No. 11/434,506, filed May 15, 2006.
U.S. Appl. No. 11/829,682, filed Jul. 27, 2007.
U.S. Appl. No. 11/488,395, filed Jul. 18, 2006.
U.S. Appl. No. 11/952,080, filed Dec. 6, 2007.

\* cited by examiner

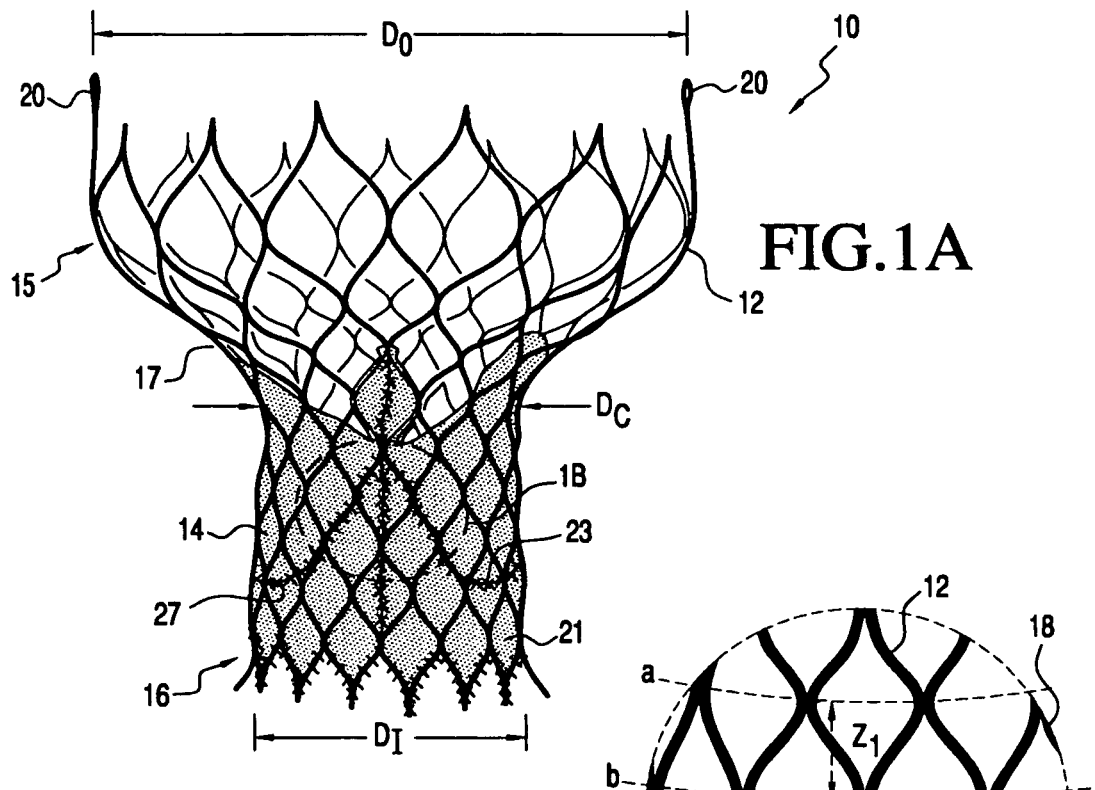
FIG.1A
FIG.1B
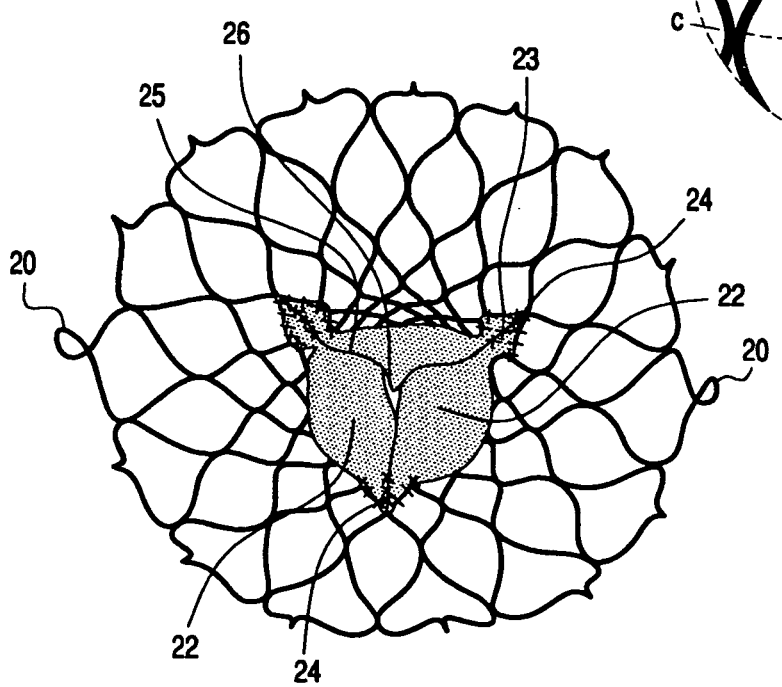
FIG.1C

HEART VALVE PROSTHESIS AND METHODS OF MANUFACTURE AND USE

RELATED APPLICATIONS

This application is a continuation-in-part of U.S. patent application Ser. No. 11/128,826, filed May 13, 2005, now U.S. Pat. No. 7,914,569.

FIELD OF THE INVENTION

The present invention relates to replacement valves for improving the cardiac function of a patient suffering from cardiac valve dysfunction, such as aortic valve regurgitation or aortic stenosis. More particularly, the present invention relates to heart valve prostheses that provide improved durability and are particularly well-suited for percutaneous delivery.

BACKGROUND OF THE INVENTION

Heart valve replacement has become a routine surgical procedure for patients suffering from valve regurgitation or stenotic calcification of the leaflets. While certain procedures may be performed using minimally-invasive techniques (so-called "keyhole" techniques), the vast majority of valve replacements entail full sternotomy and placing the patient on cardiopulmonary bypass. Traditional open surgery inflicts significant patient trauma and discomfort, requires extensive recuperation times, and may result in life-threatening complications.

To address these concerns, within the last decade efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused on percutaneous transluminal delivery of replacement cardiac valves to solve the problems presented by traditional open surgery and minimally-invasive surgical methods. In such methods, a valve prosthesis is compacted for delivery in a catheter and then advanced, for example, through an opening in the femoral artery and through the descending aorta to the heart, where the prosthesis then is deployed in the aortic valve annulus. Although transluminal techniques have attained widespread acceptance with respect to delivery of stents to restore vessel patency, only mixed results have been obtained with respect to percutaneous delivery of relatively more complicated valve prostheses.

One such example of a previously-known heart valve prosthesis is described in U.S. Pat. No. 6,454,799 to Schreck. The prosthesis described in that patent comprises a fabric-based heart valve disposed within a plastically deformable wire-mesh base, and is delivered via expansion of a balloon catheter. One drawback with balloon catheter delivery of the prosthetic valve is that the valve leaflets may be damaged when compressed between the balloon and the base during deployment. In addition, because balloon expandable structures tend to experience some recoil following balloon deflation, perivalvular leaks may develop around the circumference of the valve prosthesis.

Accordingly it would be desirable to provide a percutaneously-deliverable valve prosthesis that reduces the risk of leaflet damage during deployment of the prosthesis. It further would be desirable to provide a valve prosthesis that reduces the risk of perivalvular leaks resulting from recoil of the prosthesis following deployment.

U.S. Pat. No. 6,027,525 to Suh, et al. describes a valve prosthesis comprising a series of self-expanding units affixed to a polymeric cover and having a valve disposed therein. Such devices are not suitable for cardiac valve replacement because of the limited ability to compact the valve disposed within the prosthesis. Moreover, such valve prostheses would be particularly undesirable for treating aortic valve defects, because the polymeric cover would obscure the ostia of the coronary arteries, both disrupting blood flow to the coronary arteries and preventing subsequent catheterization of those arteries. Accordingly, it would be desirable to provide a valve prosthesis that is self-expanding, yet permits the valve to be compacted to a greater degree than previously-known designs.

U.S. Pat. No. 6,682,559 to Myers, et al. also describes a valve prosthesis having an essentially tubular design. One drawback of such configurations is that relatively large horizontal forces arise along the coaptation edges of the leaflets and are transmitted to the commissural points. These forces may adversely affect the durability of the leaflets and lead to valve failure. In view of this, it would be desirable to provide a valve wherein the center of coaptation of the leaflets may be selected so as to reduce horizontal forces applied to coaptation edges of the leaflets and commissural points, thereby improving durability of the valve. In addition, it would be desirable to provide a valve design that more uniformly distributes horizontal forces over the coaptation edges of the leaflets, rather than concentrating those forces at the commissural points.

In an effort to more nearly recreate the force distribution along the leaflets of natural tissue valves, some previously-known valve designs include circular base portions having longitudinal projections that function as anchors for the commissural points, such as described in U.S. Pat. No. 5,855,601 to Bessler, et al. and U.S. Pat. No. 6,582,462 to Andersen, et al.

While the valve prostheses of Bessler and Andersen may be readily collapsed for delivery, those designs are susceptible to problems once deployed. For example, the longitudinal projections of such prostheses may not provide sufficient rigidity to withstand compressive forces applied during normal movements of the heart. Deformation of the commissural anchors may result in varied forces being imposed on the commissures and leaflets, in turn adversely impacting functioning of the leaflets. In addition, because the exteriors of the foregoing valve prostheses are substantially cylindrical, the prostheses are less likely to adequately conform to, and become anchored within the valve annulus anatomy during deployment. As a result, cyclic loading of the valve may result in some slippage or migration of the anchor relative to the patient's anatomy.

In view of the foregoing, it would be desirable to provide a valve that is capable of conforming to a patient's anatomy while providing a uniform degree of rigidity and protection for critical valve components.

It also would be desirable to provide a valve prosthesis having portions that are capable of deforming circumferentially to adapt to the shape of the pre-existing valve annulus, but which is not susceptible to deformation or migration due to normal movement of the heart.

It further would be desirable to provide a valve prosthesis having a multi-level component that is anatomically shaped when deployed, thereby enhancing anchoring of the valve and reducing the risk of migration and perivalvular leaks.

It still further would be desirable to provide a valve prosthesis wherein the valve body is configured to facilitate fabrication, and to assume a reduced delivery profile compared to previously known designs without damaging the functional components of the valve body.

SUMMARY OF THE INVENTION

In view of the foregoing, it is an object of the present invention to provide a valve prosthesis that overcomes the drawbacks of previously-known designs, and which may be implanted using open surgical, minimally invasive, or percutaneous implantation techniques.

It is yet another object of the present invention to provide a percutaneously-deliverable valve prosthesis that exhibits a markedly reduced delivery profile over known designs.

It is also an object of the present invention to provide a percutaneously-deliverable valve prosthesis that reduces the risk of damage to the leaflets or other functional components of the valve body during delivery and deployment of the prosthesis.

It is a further object of this invention to provide a valve prosthesis that reduces the risk of perivalvular leaks resulting from elastic recoil of the prosthesis following deployment.

It is another object of the present invention to provide a valve prosthesis that is self-expanding and permits ready access to adjoining anatomical structures, such as the coronary arteries.

It is a still further object of the present invention to provide a valve in which the center of coaptation of the leaflets may be selected so as to reduce horizontal forces applied to coaptation edges of the leaflets and commissural points, thereby improving durability of the valve.

In addition, it is an object of this invention to provide a valve design that more uniformly distributes forces over the coaptation edges of the leaflets, rather than concentrating those forces at the commissural points.

It is yet another object of this invention to provide a valve that is anatomically shaped, provides a uniform high degree of rigidity and protection for critical valve components, and which is less susceptible to deformation arising from normal movement of the heart.

It is an object of the present invention to provide a valve prosthesis having portions that are capable of deforming circumferentially to adapt to the shape of the pre-existing valve annulus, but which is not susceptible to deformation or migration due to normal movement of the heart.

It is also an object of this invention to provide a valve prosthesis having a multi-level component that is anatomically shaped when deployed, thereby enhancing anchoring of the valve and reducing the risk of migration and perivalvular leaks.

It is a further object of the present invention to provide a valve prosthesis wherein a valve is disposed within a rigid portion of a multilevel frame, so that valve area and function are not impaired, but inflow and/or outflow portions of the multilevel frame are capable of conforming to patient anatomy anomalies.

It is a further object of the present invention to provide a valve prosthesis that facilitates alignment of the heart valve prosthesis with the direction of blood flow.

These and other objects of the present invention are accomplished by providing a heart valve prosthesis wherein a self-expanding multi-level frame supports a valve body comprising a skirt and plurality of coapting leaflets. The frame has a contracted delivery configuration, in which the prosthesis may be stored within a catheter for percutaneous delivery, and an expanded deployed configuration having an asymmetric hourglass shape.

In a first preferred embodiment, the valve body skirt and leaflets are constructed of porcine, bovine, equine or other mammalian tissue, such as pericardial tissue, and are sewn, welded, molded or glued together so as to efficiently distribute forces along the leaflets and to the frame. In a particularly preferred embodiment, the skirt comprises three sections of mammalian tissue that are joined along adjacent edges, so that the tissue folds easily to a collapsed delivery profile without bunching.

Alternatively, the skirt of the valve body may comprise a synthetic or polymetric material, such as Dacron, expanded polytetrafluoroethylene ("ePTFE"), or other suitable synthetic graft material. The valve body leaflets may be constructed of porcine, bovine, equine or other mammalian tissue, such as pericardial tissue, and are sewn, welded, molded or glued to the skirt so as to efficiently distribute forces along the leaflets and to the frame. The use of synthetic or polymeric materials for the valve skirt in conjunction with mammalian tissue leaflets may offer distinct advantages. In particular, the synthetic material may provide the same structural properties as the mammalian tissue but at reduced thickness, thereby enabling the valve body to be collapsed to a smaller delivery profile. Alternatively, the leaflets also may comprise a synthetic or polymeric material.

In accordance with the principles of the present invention, the frame comprises multiple levels, including a proximal conical inflow section, a constriction region and a flared distal outflow section. Each of the inflow and outflow sections is capable of deforming to a non-circular cross-section to conform to the patient's anatomy, while the constriction region is configured to retain a circular cross-section that preserves proper functioning of the valve body.

The frame comprises a plurality of cells having a pattern that varies along the length of the frame to provide a high degree of anchoring and alignment of the valve prosthesis. The cell pattern further is selected to provide a uniform diameter where the commissural joints of the leaflets are attached to the frame, while permitting the inflow and outflow regions to expand to conform to the patient's anatomy. In this manner, optimal functioning of the valve body may be obtained even though the frame may be deployed in anatomies having a range of sizes. In addition, the frame resists deformation caused by movement of the heart and enables a functional portion of the valve body to be disposed supra-annularly to the native valve, with a portion of the valve prosthesis extending into the native valve annulus.

In one embodiment suitable for aortic valve replacement, the valve body comprises a skirt coupled to three leaflets. The components may be formed of animal pericardial tissue or synthetic material, and are sewn, glued, welded or molded together. The lateral ends of the leaflets include enlarged regions that are folded to both form the commissural joints and fasten the commissural joints to the frame. The skirt and leaflets further are configured so that the joints align with contours of the cell pattern of the frame.

In a preferred embodiment, the commissural joints are affixed to the frame at locations above the area of coaptation, to provide a selectable center of coaptation of the leaflets. This design provides a more efficient delivery configuration because the commissures are not compressed against the leaflets when the valve prosthesis is reduced to the contracted delivery configuration. Additionally, by lengthening the distance to the commissures, the design mimics the functioning of natural tissue valves by distributing forces along the coaptation edges and reducing horizontal forces transmitted to the commissural joints.

In alternative embodiments, the valve body of the present invention may include a sewing ring in lieu of the frame to facilitate surgical implantation, and may employ as few as two and as many as four leaflets.

Methods of making and using the valve prostheses of the present invention are also provided.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which:

FIGS. 1A, 1B and 1C are, respectively, side and top end views of an exemplary valve prosthesis of the present invention in the expanded deployed configuration and an enlarged region of the frame of the valve prosthesis;

DETAILED DESCRIPTION OF THE INVENTION

Figure 2:
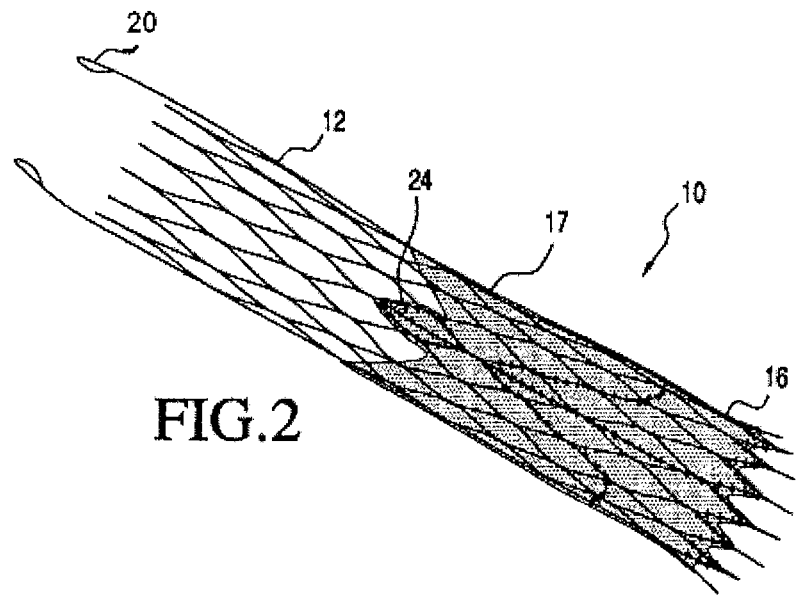
FIG. 2 is a side view of the frame of the valve prosthesis of FIG. 1 in a contracted delivery configuration.

The present invention is directed to a heart valve prosthesis having a self-expanding frame that supports a valve body. In a preferred embodiment, the frame has a tri-level asymmetric hourglass shape with a conical proximal section, an enlarged distal section and a constriction region having a predefined curvature when the frame is deployed. In the context of the present application, the proximal section constitutes the "inflow" portion of the valve prosthesis and is disposed in the aortic annulus of the patient's left ventricle, while the distal section constitutes the "outflow" portion of the valve prosthesis and is positioned in the patient's ascending aorta.

In a preferred embodiment the valve body comprises three leaflets that are fastened together at enlarged lateral end regions to form commissural joints, with the unattached edges forming the coaptation edges of the valve. The leaflets are fastened to a skirt, which is in turn affixed to the frame. The enlarged lateral end regions of the leaflets permit the material to be folded over to enhance durability of the valve and reduce stress concentration points that could lead to fatigue or tearing of the leaflets. The commissural joints are mounted above the plane of the coaptation edges of the valve body to minimize the contracted delivery profile of the valve prosthesis, while the configuration of the edges permits uniform stress distribution along the coaptation edges.

Referring to FIG. 1, an exemplary embodiment of a valve prosthesis constructed in accordance with the principles of the present invention is described. Valve prosthesis 10 comprises expandable frame 12 having valve body 14 affixed to its interior surface, e.g., by sutures. Frame 12 preferably comprises a self-expanding structure formed by laser cutting or etching a metal alloy tube comprising, for example, stainless steel or a shape memory material such as nickel titanium. The frame has an expanded deployed configuration that is impressed upon the metal alloy tube using techniques that are per se known in the art. Valve body 14 preferably comprises individual leaflets assembled to a skirt. All of the components of valve body 14, i.e., the skirt and leaflets, may be formed of a natural or man-made material. Alternatively, the leaflets may be formed from a natural material, such as porcine, equine or bovine pericardium, while the skirt comprises a synthetic or polymeric material, such as Dacron, ePTFE, or similar material.

Frame 12 preferably includes multiple levels, including outflow section 15, inflow section 16 and constriction region 17. As depicted in the enlarged view of FIG. 1B, the frame comprises a plurality of cells having sizes that vary along the length of the prosthesis. As indicated by dotted lines a, b and c, each cell comprises two zig-zag structures having unequal-length struts, wherein the vertices of the zig-zags are coupled together. For example, zig-zag 18 has length $z_1$ whereas zig-zag 19 has greater length $z_2$. This cell design permits each level of cells between the proximal and distal ends of the frame to be tailored to meet specific design requirements, such as, compressibility, expansion characteristics, radial strength and so as to define a suitable contour for attachment of the valve body.

The cell pattern of frame 12 also enables the frame to expand to the tri-level asymmetric hourglass shape depicted in FIG. 1A, having conical inflow section, enlarged outflow section and fixed diameter constricted region. Each section of frame 12 has a substantially circular cross-section in the expanded deployed configuration, but in addition the cell patterns of the inflow and outflow sections permit those sections to adapt to the specific anatomy of the patient, thereby reducing the risk of migration and reducing the risk of perivalvular leaks. The cell patterns employed in the constriction region are selected to provide a uniform circular cross-section area for the constriction region when deployed, and a pre-determined radius of curvature for the transition between the constriction region and outflow section of the frame. In particular, the convex-concave shape of frame 12 within the constriction region ensures that the frame is held away from the opposing sinus wall in the ascending aorta, thus ensuring adequate blood flow to the coronary arteries and facilitating catheter access to the coronary arteries.

Enlarged outflow section has nominal deployed diameter $D_o$, inflow section has nominal deployed diameter $D_I$, and constriction region has deployed substantially fixed diameter $D_c$. The conical shape of the inflow region and smooth transitions between adjacent sections of frame 12 are expected to be particularly advantageous in directing blood flow through the valve body with little or no turbulence, as compared to step changes in diameter observed for surgically implanted replacement valves.

The above-described cell pattern permits each of the inflow and outflow sections of frame 12 to expand to a diameter within a range of deployed diameters, while retaining constriction region 17 at a substantially constant diameter. Thus, for example, outflow diameter $D_o$ may range from 30 to 55 mm, while inflow diameter $D_I$ may vary from 19 to 34 mm. Illustratively, frame 12 may be manufactured in four sizes having a range of diameters $D_o$, $D_I$ and $D_c$ as set forth in Table 1 below:

TABLE 1

|  | Size A | Size B | Size C | Size D |
|---|---|---|---|---|
| $D_o$ | 40 mm | 50 mm | 40 mm | 50 mm |
| $D_c$ | 22 mm | 22 mm | 24 mm | 24 mm |
| $D_I$ | 26 mm | 26 mm | 29 mm | 29 mm |

Advantageously, these four frame sizes are expected to cover a wide range of patient anatomies, while requiring construction of only two sizes of valve bodies (22 and 24 mm). Compared to previously-known commercially available surgical valves, which vary from approximately 17 mm to 31 mm in one millimeter increments, it is expected that the above four sizes of valve prosthesis of the present invention could be used for more than 75% of the patient population, thus greatly reducing the costs associated with manufacturing and inventorying large numbers of parts.

When configured as a replacement for an aortic valve, inflow section 16 extends into and anchors within the aortic annulus of a patient's left ventricle and outflow section 15 is positioned in the patient's ascending aorta. Importantly, the configuration of outflow section 15 is expected to provide optimal alignment of the valve body with the direction of blood flow. In addition, the cell pattern of outflow section 15 also serves to anchor the outflow section in the patient's ascending aorta to prevent lateral movement or migration of frame 12. As depicted in FIG. 1C, the use of relatively larger cells in the outflow section of frame 12, combined with the convex-concave shape of constriction region 17, ensures that the frame does not obstruct blood flow to the patient's coronary arteries when deployed and allows for catheter access to the coronary arteries. Frame 12 also may include eyelets 20 for use in loading the heart valve prosthesis 10 into a delivery catheter.

Still referring to FIG. 1, valve body 14 includes skirt 21 affixed to frame 12, and leaflets 22. Leaflets 22 are attached along their bases to skirt 21, for example, using sutures 23 or a suitable biocompatible adhesive. Adjoining pairs of leaflets are attached to one another at their lateral ends to form commissures 24, with free edges 25 of the leaflets forming coaptation edges that meet in area of coaptation 26.

As depicted in FIG. 1A, the curve formed at joint 27 between the base of each leaflet 22 and skirt 21 follows the contour of the cell pattern of frame 12, so that most of the length of joint 27 is directly supported by frame 12, thereby transmitting forces applied to the valve body directly to the frame. As further depicted in FIG. 1C, commissures 24 are configured to span a cell of frame 12, so that force is evenly distributed within the commissures and to frame 12.

Referring to FIG. 2, valve prosthesis 10 is shown in the contracted delivery configuration. In this state, valve prosthesis may be loaded into a catheter for percutaneous transluminal delivery via a femoral artery and the descending aorta to a patient's aortic valve. In accordance with one aspect of the present invention, commissures 24 are disposed longitudinally offset from coaptation edges 25 of the valve body, thereby permitting a smaller delivery profile than achievable with previously-known replacement valves. In addition, because frame 12 self-expands upon being released from the delivery catheter, there is no need to use a balloon catheter during placement of valve prosthesis 10, thereby avoiding the potential for inflicting compressive injury to the valve leaflets during inflation of the balloon.

Figure 3A:
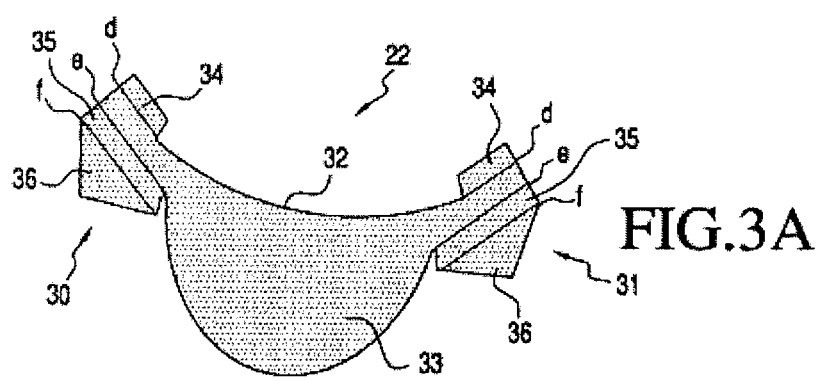
FIGS. 3A and 3B are, respectively, plan views of a leaflet and the skirt employed in the valve body of the present invention.
Figure 3B:
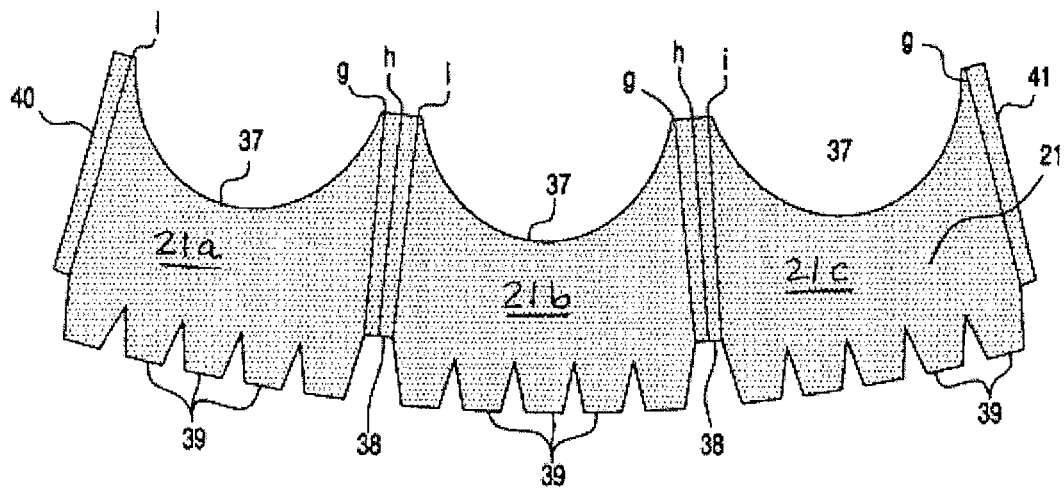

Referring now to FIGS. 3A and 3B, skirt 21 and leaflet 22 of a preferred aortic valve embodiment of the present invention are described. In one preferred embodiment, skirt 21 and leaflet 22 are cut from a sheet of animal pericardial tissue, such as porcine pericardial tissue, either manually or using a die or laser cutting system. The pericardial tissue may be processed in accordance with tissue processing techniques that are per se known in the art for forming and treating tissue valve material. In a preferred embodiment, skirt 21 and leaflets 22 have a thickness of between 0.008" and 0.016", and more preferably between 0.012" and 0.014".

In an alternative preferred embodiment, leaflets 22 are formed from animal pericardial tissue as described above, while skirt 21 is cut from a sheet of synthetic or polymer material, such as Dacron, ePTFE, or other similar material as known in the art. In this case, skirt 21 has a thickness of between 0.004" and 0.012", and more preferably between 0.006" and 0.008", and may thus be compressed to a substantially smaller delivery profile. Alternatively, skirt 21 and leaflets 22 may be constructed of a synthetic or polymeric material.

Leaflet 22 includes enlarged lateral ends 30 and 31 disposed at either end of free edge 32, and body 33. Free edge 32 forms coaptation edge 25 of the finished valve body 14, while lateral ends 30 and 31 are folded and joined to adjacent leaflets to form commissures 24. In accordance with one aspect of the present invention, free edges 32 assume the form of catenaries when the valve body is affixed to frame 12, thereby providing uniform loading along the length of the coaptation edge in a manner similar to a suspension bridge. Body 33 is joined to skirt 21 as described below. Lateral ends 30 and 31 illustratively are shown in FIG. 3A as having fold lines d, e and f, to define flaps 34, 35 and 36.

In the embodiment of FIG. 3B, skirt 21 includes panels 21a, 21b and 21c, each panel having scalloped area 37, reinforcing tab 38, and end tab 39. Scalloped area 37 or each panel 21a, 21b and 21c is joined to a body 33 of a respective leaflet 22. Reinforcing tabs 38 illustratively include fold lines g, h and i, between panels 21a-21b and 21b-21c, except for reinforcing tabs 40 and 41 at the lateral ends of the panels 21a and 21c, which have only one fold apiece. As described below, reinforcing tabs 40 and 41 are joined to one another, e.g., by sutures or gluing, so that skirt 21 forms a frustum of a cone. In one preferred embodiment, panels 21a, 21b and 21c are cut conjoined from a single piece of animal pericardium, as depicted in FIG. 3B.

End tabs 39 are folded over the ends of the proximal-most row of cells of frame 12 to secure skirt 21 to the frame and seal against perivalvular bypass flows (see FIG. 1A). Because end tabs 39 are directly supported by the last zig-zag row of cells of frame 12, there is no opportunity for an unsupported edge of the skirt to flap or otherwise extend into the flow path along the inflow edge of skirt 21. Thus, the design of the valve prosthesis not only ensures that there are no flaps to disrupt flow or serve as sites for thrombus formation, but also reduces the risk that hemodynamic flow against such flaps could cause frame 12 to migrate.

It has been observed that when panels 21a-21c are cut conjoined from a single piece of animal pericardium, the skirt has a tendency to bunch-up or "accordion" when the valve body is collapsed to its reduced delivery configuration. However, applicants have discovered that if panels 21a-21c are severed along fold lines h in FIG. 3B, or individually cut from a piece of animal pericardium, this phenomenon is not observed, and the skirt can be collapsed to a substantially smaller profile. In particular, whereas a tissue-based skirt comprising conjoined panels 21a-21c, as shown in FIG. 3B, fits within a 21 French delivery catheter, forming skirt 21 of individual panels 21a-21c enables the device to fit within an 18 French catheter, resulting in a reduction in the delivery profile of about twenty-five percent (25%).

As a still further alternative, skirt 21 may be formed of a synthetic or polymeric material, such as Dacron, ePTFE, or similar material selected for its properties and biocompatibility. As opposed to leaflets 22, which provide a mechanical function through movement, skirt 21 functions primarily to create a seal to prevent perivalvular leaks. Accordingly, a thin synthetic material may be used in place of thicker mammalian tissue to serve this purpose. As a result, the device may be compacted to a reduced delivery profile by virtue of the decreased volume of the skirt. For example, use of a synthetic skirt with a valve body having tissue-based leaflets may enable the device to fit within a catheter having even less than an 18 French diameter.

Figure 4A:
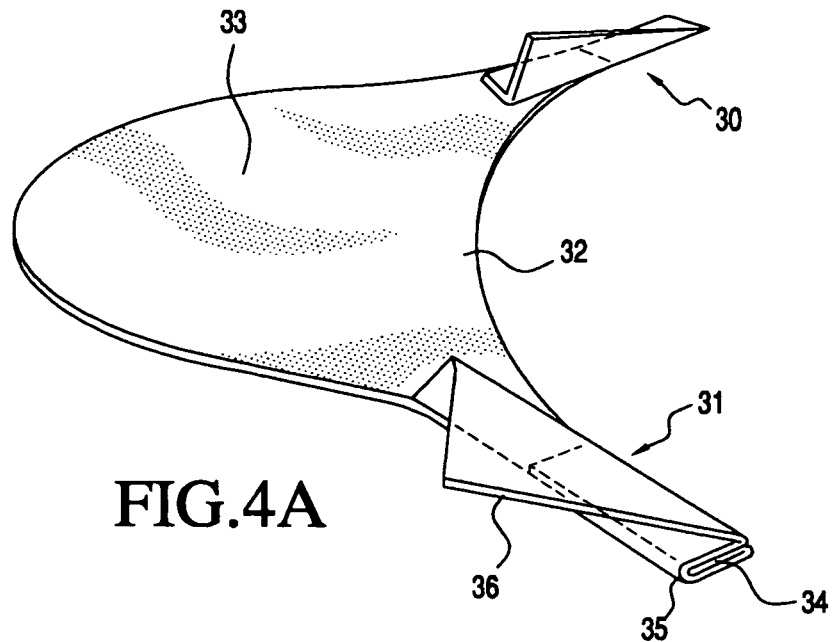
FIGS. 4A, 4B, 4C, and 4D are, respectively, a perspective view of a leaflet with its enlarged regions folded, a plan view of an embodiment of the valve body of the present invention in which the leaflets are fastened to the skirt, a perspective view of an alternative embodiment of a skirt, and a perspective view of another alternative embodiment of a skirt.
Figure 4B:
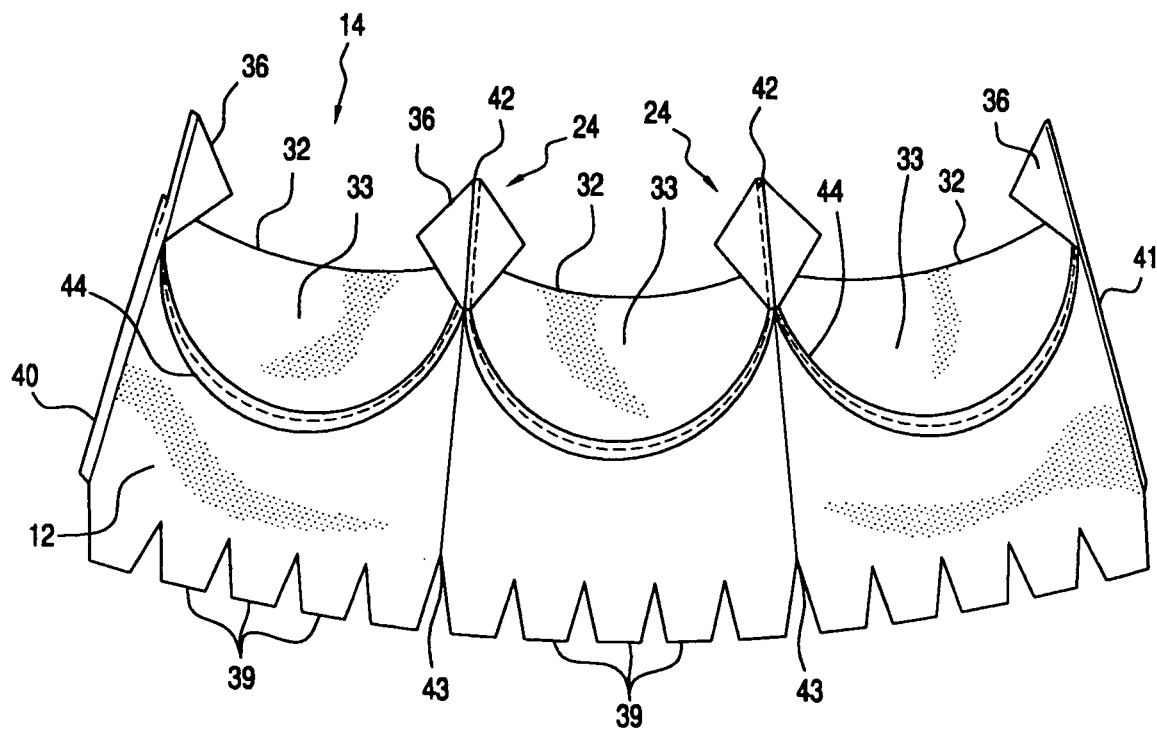

Referring to FIGS. 4A and 4B, assembly of valve body 14 from the above-described embodiments of skirt 21 and leaflets 22 is described. In FIG. 4A, flap 34 first is folded along line d. Flap 35 is folded along line e so that it lies atop flap 34, forming seam 42 comprising a triple thickness of the tissue. Flap 36 then is folded along line f. Adjoining leaflets 22 then are fastened together along adjacent seams 42, resulting in a leaflet assembly.

Reinforcing tabs 38 are folded along lines g, h and i to form seams 43 comprising a double thickness of tissue, or in the case of separate panels 21a-21c, joined to form seams along tabs 38. Next, the leaflet assembly is attached to skirt 21 along the bottom edges of bodies 33 of the leaflets to form joints 44. At this stage of the assembly, prior to attaching reinforcing tab 40 to 41 and the remaining seam 42 of leaflets 22, the valve body appears as depicted in FIG. 4B. Reinforcing tabs 40 and 41 then are fastened together to form another seam 43 along skirt 21 and the remaining seam 42 between leaflets 22. Valve body 14 then is ready to be affixed to frame 12.

Figure 4C:
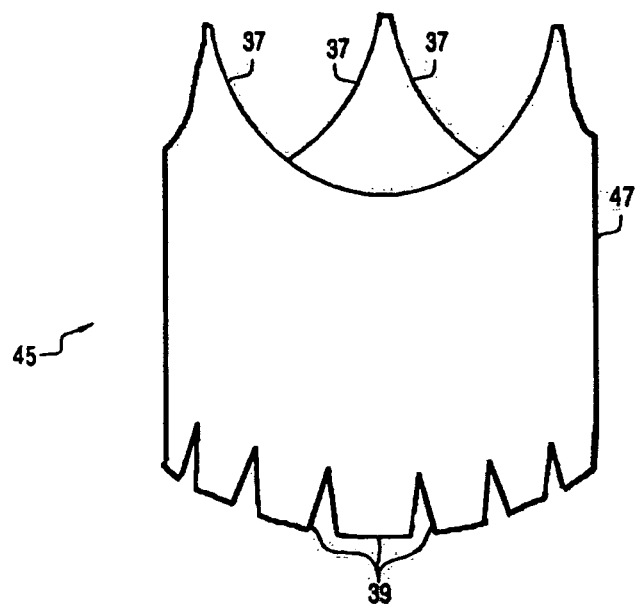

Referring to FIG. 4C, alternative embodiment of a synthetic skirt for a valve body of the present invention is described. Skirt 45 of FIG. 4C is formed from tube 47 of commercially available synthetic material, such as described above. Tube 47 is cut at one end to form scalloped areas 37, while notches are cut at the other end of the tube to form end tabs 39. Leaflets 22, which may comprise natural or synthetic material, then are assembled and attached to skirt 45 in a manner similar to that described above. Because skirt 45 is essentially cylindrical, it preferably comprises a material that is sufficiently flexible to stretch to conform to the desired shape of frame when end tabs 39 are attached to frame 12.

Figure 4D:
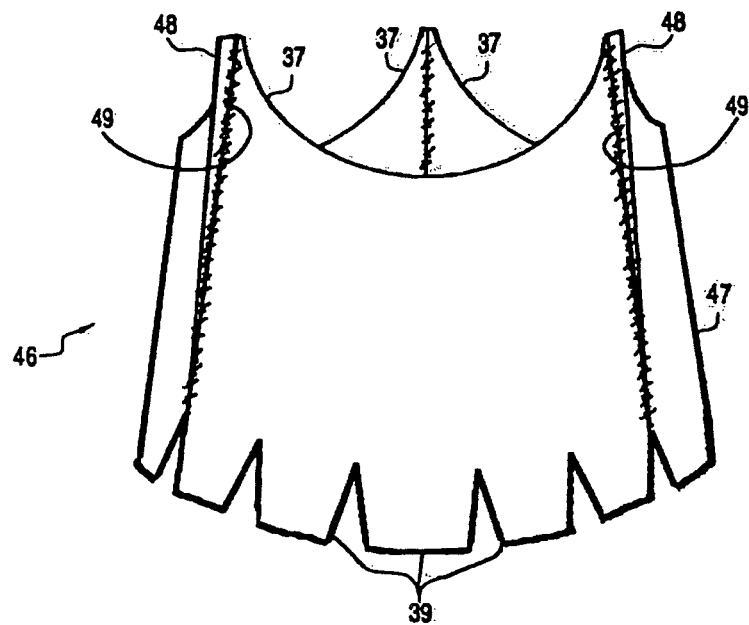

In FIG. 4D, another alternative embodiment of a synthetic skirt for a valve body of the present invention is described. In this case, the skirt first is cut from tube 47 into a shape shown in FIG. 4C, and then formed into a shape resembling the frustum of a cone by creating triangular pleats 48. In particular, prior to the attachment of a leaflet assembly, the apices of the scalloped areas 37 are folded upon themselves and joined, such as by sewing, bonding, welding, molding, or gluing together to form pleats 48. As illustrated in FIG. 4D, pleats 48 may be formed by seams 49, and may have a width selected to impart any desired amount of taper to the skirt 46. The leaflets then may be assembled and attached to the skirt, and the valve body attached to frame 12, as described above. Advantageously, pleats 48 provides strengthened attachment points to secure skirt 46 to frame 12.

Figure 5:
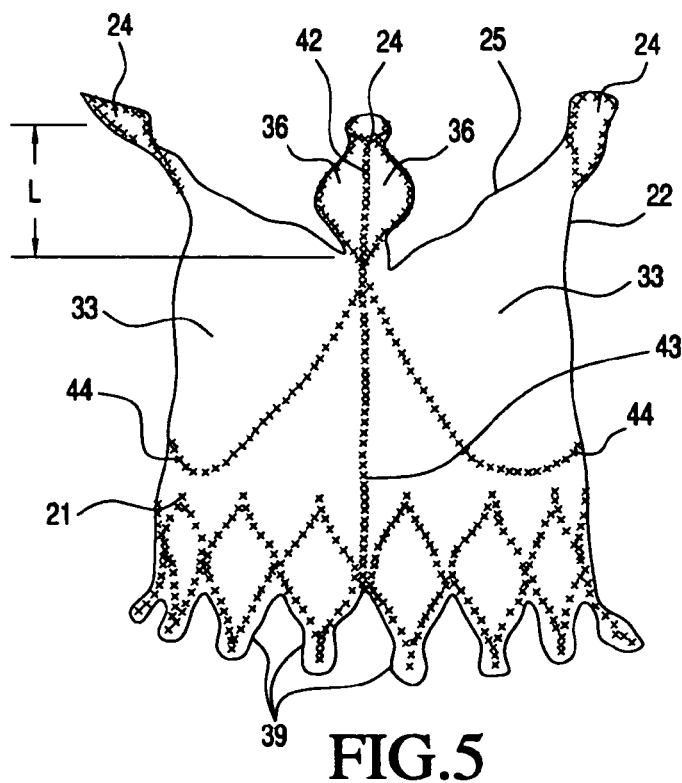
FIG. 5 is a side view of the valve body of FIG. 4B fully assembled.

Referring to FIG. 5, valve body 14 is shown as it would appear when affixed to frame 12, but with frame 12 omitted to better illustrate where the valve body is affixed to the frame. During the step of affixing the valve body to the frame, flaps 36 of adjacent leaflets are affixed, e.g., by sutures, to span a cell of the frame to support commissures 24 (compare to FIG. 1B) and end tabs 39 are folded over and affixed to the proximal-most row of cells of the frame 12 (compare to FIG. 1A). Valve body 14 also is attached to frame 12 along seams 43 formed by the reinforcing tabs. Each joint 44 is aligned with and fastened to (e.g., by sutures or glue) to a curved contour defined by the struts of the cells of frame 12, so that joint 44 is affixed to and supported by frame 12 over most of the length of the joint. As discussed above, the configuration of the cells in frame 12 may be specifically customized define a curved contour that supports joints 44 of the valve body.

When completed assembled to frame 12, valve body 14 is affixed to frame 12 along the edges of flaps 36 of the commissures, end tabs 39, leaflet seams 42, reinforcing tab seams 43 and joints 44. In this manner, forces imposed on leaflets 22, commissures 24 and joints 44 are efficiently and evenly distributed over the valve body and transferred to frame 12, thus reducing stress concentration and fatigue of the valve body components. Moreover, the use of multiple thicknesses of material along seams 42 and 43 is expected to provide a highly durable valve body that will last for many years once implanted in a patient.

In accordance with another aspect of the present invention, the center of coaptation of leaflets 22 is a distance L below the point at which the commissures are affixed to the frame, as shown in FIG. 5. Compared to previously-known designs, in the present invention the overall lengths of the coaptation edges are increased, while leaflets 22 coapt along a shorter portion of those lengths. Several advantages arise from this design:

the leaflets require only minimal pressure to open and have a rapid closing time.

the valve demonstrates better washing dynamics when open, i.e., less turbulence along the free edges of the leaflets.

the valve provides a more uniform distribution of stresses along the coaptation edges of leaflets 22.

the angle at which force is transmitted to the commissures is increased, thereby substantially reducing the horizontal forces applied to the commissures that tend to pull the commissures away from the frame.

controlling the center of the height of coaptation allows the commissures to be located distal to the center of coaptation, thereby reducing the contracted delivery profile of the valve prosthesis.

All of the foregoing benefits are expected to reduce non-uniform loads applied to the valve body, and substantially enhance the durability of the valve prosthesis.

As will of course be apparent to one of skill in the art of prosthetic valve design, the assembly steps described above are merely illustrative, and a different order of assembling the leaflets and skirt to form valve body 14 may be employed. In an alternative embodiment, a conventional sewing ring may be attached to valve body 14 and frame 12 may be omitted. In this case, the valve prosthesis may be implanted surgically, rather than by percutaneous transluminal delivery. In this case, commissures 24 may be attached to the ascending aorta by sutures or other means as described above.

Figure 6:
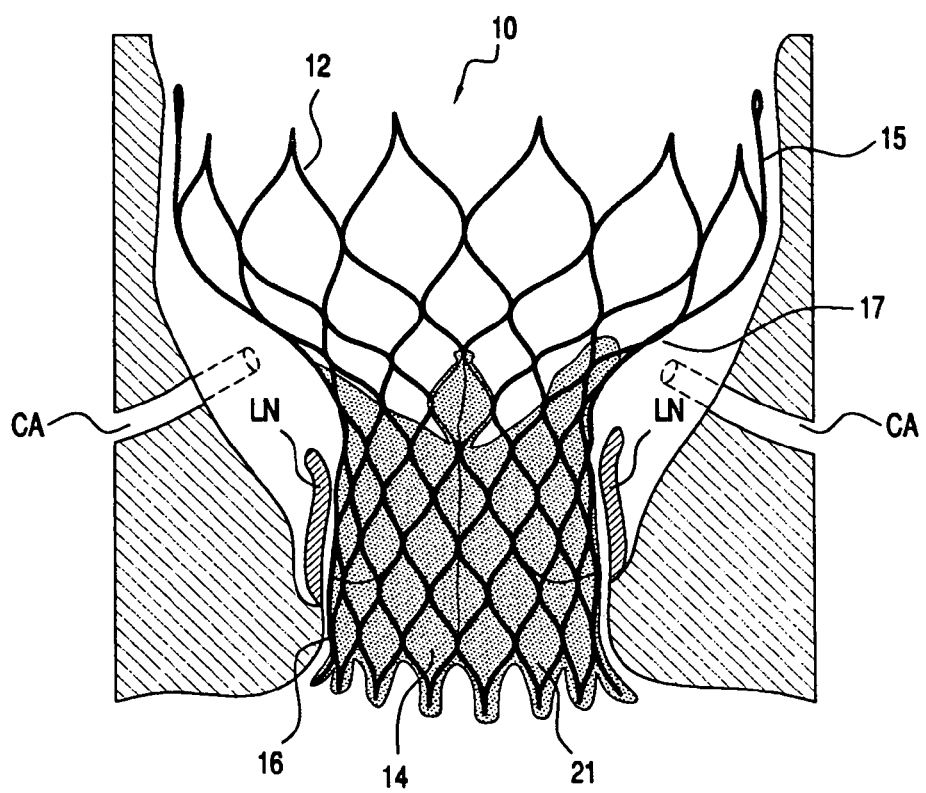
FIG. 6 is a side view depicting the valve prosthesis of the present invention deployed atop a patient's aortic valve.

Referring now to FIG. 6, implantation of valve prosthesis 10 of the present invention is described and is shown having skirt 46 from FIG. 4D. As discussed above, valve prosthesis preferably comprises a self-expanding multilevel frame that may be compressed to a contracted delivery configuration, as depicted in FIG. 3, onto an inner member of a delivery catheter. The valve prosthesis and inner member may then be loaded into a delivery sheath of conventional design, e.g., having a diameter of 18-20 French or less. Due in part to the fact that commissures 24 are longitudinally offset from the coaptation edges of the leaflets, the ability to customize the cell pattern along the length of the frame, and the construction of the skirt, it is expected that valve prosthesis may be designed to achieve a significantly smaller delivery profile than previously-known percutaneously-deliverable replacement valves.

The delivery catheter and valve prosthesis are then advanced in a retrograde manner through a cut-down to the femoral artery and into the patient's descending aorta. The catheter then is advanced, under fluoroscopic guidance, over the aortic arch, through the ascending aorta and mid-way across the defective aortic valve. Once positioning of the catheter is confirmed, the sheath of the delivery catheter may be withdrawn proximally, thereby permitting the valve prosthesis to self-expand.

As the valve prosthesis expands, it traps native leaflets LN of the patient's defective aortic valve against the valve annulus, retaining the native valve in a permanently open state. As further illustrated in FIG. 6, outflow section 15 of the valve prosthesis expands against, and aligns the prosthesis within, the ascending aorta, while inflow section 16 becomes anchored in the aortic annulus of the left ventricle, so that skirt 21 reduces the risk of perivalvular leaks.

As also seen in FIG. 6, the deployed configuration of constriction region 17 holds valve body 14 in a supra-annular position, away from the heart walls, thereby ensuring that the constriction region expands to the predetermined fixed diameter. This in turn ensures that the valve body does not experience any unexpected lateral loads and therefore expands to its design diameter, e.g., illustratively either 22 or 24 mm as in Table 1 above.

Because outflow section 15 of frame 12 employs relatively larger cells than the remainder of the frame, valve prosthesis 10 does not disrupt blood flow into coronary arteries CA when deployed, and also does not obstruct subsequent catheter access to the coronary arteries. Accordingly, a clinician may readily gain access to the coronary arteries, for example, to perform angioplasty or stenting, simply by directing the angioplasty or stent delivery system guide wire through the openings in the cell pattern of frame 12.

While preferred embodiments of the invention are described above, it will be apparent to one skilled in the art that various changes and modifications may be made. The appended claims are intended to cover all such changes and modifications that fall within the true spirit and scope of the invention.

What is claimed is:

1. A valve prosthesis comprising:
   a self-expanding multi-level frame having a contracted delivery configuration and an expanded deployed configuration, and a cell pattern that defines contours, wherein the cell pattern includes a plurality of cells having sizes that vary along the length of the prosthesis, the cell pattern defined by struts; and
   a valve body affixed to the multi-level frame, the valve body comprising a plurality of leaflets affixed to a skirt at joints, wherein the valve body has a center of coaptation, wherein adjoining leaflets form commissures, wherein the commissures are affixed to the multi-level frame at a location distal of the center of coaptation, and wherein the commissures include flaps that span an entire area of at least one cell of the cell pattern;
   wherein the joints include curved portions between a curved base of each leaflet and a scalloped upper edge of the skirt, wherein the curved portions curve longitudinally towards and away from a proximal end of the multi-level frame, wherein the curved portions are aligned with and directly affixed to a curved contour of the multi-level frame defined by the struts of the cells of the multi-level frame so that most of the length of the joints is directly supported by the frame to evenly distribute forces through the valve body to the multi-level frame.

2. The valve prosthesis of claim 1 wherein the cell pattern is defined by unequal length zig-zags.

3. The valve prosthesis of claim 1
   wherein each leaflet has a free edge defining a catenary configured to reduce horizontal loads applied to the commissures.

4. The valve prosthesis of claim 1
   wherein each leaflet is individually formed and adjoining leaflets are sewn together to form the commissures; and
   wherein each leaflet comprises an enlarged lateral end having a plurality of flaps that are folded over to increase the durability of the commissures.

5. The valve prosthesis of claim 1 wherein the leaflets comprise porcine, bovine, equine or other mammalian pericardial tissue, synthetic material or polymeric material.

6. The valve prosthesis of claim 1 wherein when the valve prosthesis is delivered within a patient's aortic valve and the multi-level frame is in the expanded deployed configuration, the valve body is located supra-annularly of the patient's aortic annulus.

7. The valve prosthesis of claim 1 wherein the multi-level frame is configured to hold a patient's native valve permanently open in the expanded deployed configuration.

8. The valve prosthesis of claim 1 wherein the multi-level frame is configured to permit access to a patient's coronary arteries in the expanded deployed configuration.

9. The valve prosthesis of claim 1 wherein the skirt comprises a synthetic material.

10. The valve prosthesis of claim 9 wherein the skirt has a tubular shape in an undeformed configuration.

11. The valve prosthesis of claim 10 wherein the skirt is configured in conical frustum shape formed by deforming the synthetic material.

12. The valve prosthesis of claim 1 wherein the skirt comprises two or more individual panels of animal pericardial material.

13. The valve prosthesis of claim 1 wherein the skirt comprises two or more conjoined panels of animal pericardial material.

14. The valve prosthesis of claim 1, wherein the multi-level frame in the expanded deployed configuration has an enlarged outflow section with a first diameter, an inflow section having a second diameter, and a constriction section having a third diameter smaller than the first diameter.

15. The valve prosthesis of claim 14, wherein the plurality of cells of the multi-level frame are configured to provide a pre-determined radius of curvature for a transition from the constriction section to the outflow section.

16. The valve prosthesis of claim 14, wherein the first diameter is between 30 mm and 55 mm and the second diameter is between 19 mm and 34 mm.

17. The valve prosthesis of claim 16, wherein the third diameter is 22 mm.

18. The valve prosthesis of claim 16, wherein the third diameter is 24 mm.

19. The valve prosthesis of claim 1, wherein the multi-level frame in the expanded deployed configuration has an enlarged outflow section with a first diameter, an inflow section having a second diameter smaller than the first diameter, and a constriction section having a third diameter smaller than the first and second diameters.

20. The valve prosthesis of claim 19 wherein the inflow section flares outward towards the proximal end of the multi-level frame.

21. The valve prosthesis of claim 19, wherein transitions between the enlarged outflow section, the constriction section, and the inflow section define a smooth radial curvature.

22. A valve prosthesis comprising:
a self-expanding multi-level frame having a contracted delivery configuration and an expanded deployed configuration, and a cell pattern that defines contours, wherein the cell pattern includes a plurality of cells having sizes that vary along the length of the prosthesis, the cell pattern defined by struts; and
a valve body affixed to the multi-level frame, the valve body comprising a plurality of leaflets affixed to a skirt at joints;
wherein the joints include curved portions between a curved base of each leaflet and a scalloped upper edge of the skirt, wherein the curved portions curve longitudinally towards and away from a proximal end of the multi-level frame, wherein the curved portions are aligned with and directly affixed to a curved contour of the multi-level frame defined by the struts of the cells of the multi-level frame so that most of the length of the joints is directly supported by the frame to evenly distribute forces through the valve body to the multi-level frame, and
wherein the skirt further comprises a plurality of longitudinally-oriented reinforcing tabs or pleats.

23. The valve prosthesis of claim 22 wherein the reinforcing tabs or pleats are affixed to the multi-level frame.

24. The valve prosthesis of claim 22 wherein the skirt further comprises a plurality of end tabs adapted to be affixed to a proximal-most row of cells of the multi-level frame.

25. A valve prosthesis comprising:
a self-expanding multi-level frame having a contracted delivery configuration and an expanded deployed configuration, and a cell pattern that defines contours, wherein the cell pattern includes a plurality of cells having sizes that vary along the length of the prosthesis, the cell pattern defined by struts; and
a valve body affixed to the multi-level frame, the valve body comprising a plurality of leaflets affixed to a skirt at joints;
wherein the joints include curved portions between a curved base of each leaflet and a scalloped upper edge of the skirt, wherein the curved portions curve longitudinally towards and away from a proximal end of the multi-level frame, wherein the curved portions are aligned with and directly affixed to a curved contour of the multi-level frame defined by the struts of the cells of the multi-level frame so that most of the length of the joints is directly supported by the frame to evenly distribute forces through the valve body to the multi-level frame,
wherein the skirt comprises a synthetic material, the skirt has a tubular shape in an undeformed configuration, the skirt is configured in a conical frustum shape formed by deforming the synthetic material, and wherein the conical frustum shape is formed by creating a plurality of longitudinally-oriented pleats in the synthetic material.

* * * * *